US00PP17055P3

(12) United States Plant Patent
Redman

(10) Patent No.: US PP17,055 P3
(45) Date of Patent: Aug. 22, 2006

(54) ***CHRYSANTHEMUM* PLANT NAMED 'BRIDAL TIME'**

(50) Latin Name: *Chrysanthemum morifolium*
Varietal Denomination: Bridal Time

(75) Inventor: Ruth Redman, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 0 days.

(21) Appl. No.: 11/146,390

(22) Filed: Jun. 6, 2005

(65) Prior Publication Data

US 2005/0273896 P1 Dec. 8, 2005

Related U.S. Application Data

(60) Provisional application No. 60/578,017, filed on Jun. 7, 2004.

(51) Int. Cl.
*A01H 5/00* (2006.01)

(52) U.S. Cl. ..... Plt./294

(58) Field of Classification Search ..... Plt./294
See application file for complete search history.

(56) References Cited

U.S. PATENT DOCUMENTS

| | | | | |
|---|---|---|---|---|
| PP15,535 | P2 | 2/2005 | Boeder | Plt./294 |
| 2002/0129419 | P1 | 9/2002 | Boeder | Plt./294 |

*Primary Examiner*—Kent Bell
*Assistant Examiner*—Annette H Para
(74) *Attorney, Agent, or Firm*—Winston & Strawn, LLP

(57) ABSTRACT

A new variety of *Chrysanthemum* plant named 'Bridal Time', having a good uniform canopy of large white flowers with a dark green disc. The new variety has a uniform spreading habit with a good foliage presentation.

1 Drawing Sheet

Latin name of the genus and species: Botanical classification: *Chrysanthemum morifolium.*

Variety denomination: The new *Chrysanthemum* variety denomination is 'Bridal Time'.

BACKGROUND OF THE INVENTION

The present invention comprises a new and distinct cultivar of *chrysanthemum* botanically known as *Chrysanthemum morifolium* and referred to by the variety name 'Bridal Time'.

'Bridal Time', identified as '22075-0', originated from a cross made in a controlled breeding program in Chichester, West Sussex, United Kingdom. The female parent of the new variety is '20829-0' (unpatented seedling) and the male parent is the variety known as 'Cool Time' (U.S. Plant patent application Publication No. 2002/0129416).

The new variety 'Bridal Time' has been asexually reproduced by vegetative cuttings in Chichester, West Sussex, United Kingdom, and the distinguishing characteristics are retained through successive generations of asexual reproduction.

BRIEF SUMMARY OF THE INVENTION

'Bridal Time' is a pot type of *Chrysanthemum* plant variety having large white single flowers with a green disc.

Comparison with Female Parent

Plants of the new *Chrysanthemum* variety 'Bridal Time' are dissimilar to the parent variety '20829-0' in plant habit and growth rate. In side-by-side comparisons in Chichester, West Sussex, United Kingdom, under commercial practice, plants of the new *chrysanthemum* variety 'Bridal Time' differed from plants of the parent '20829-0' in the following characteristics:

1. The new variety 'Bridal Time' produces white single flowers whereas the parent '20829-0' produces lemon single flowers.
2. Plants of the new variety 'Bridal Time' have larger and taller inflorescence than plants of the parent '20829-0'.

Comparison with Male Parent

Plants of the new *Chrysanthemum* variety 'Bridal Time' are dissimilar to the parent variety 'Cool Time' in plant habit and growth rate. In side-by-side comparisons in Chichester, West Sussex, United Kingdom, under commercial practice, plants of the new *chrysanthemum* variety 'Bridal Time' differed from plants of the parent 'Cool Time' in the following characteristics:

1. The new variety 'Bridal Time' produces large white single flowers whereas the parent 'Cool Time' produces medium white single flowers.
2. Plants of the new variety 'Bridal Time' have larger and taller inflorescence than plants of the parent 'Cool Time'.
3. Plants of the new variety 'Bridal Time' have a quicker response than plants of the parent 'Cool Time'.

Comparison with 'Stereophonics'

Plants of the new *Chrysanthemum* variety 'Bridal Time' are dissimilar to the variety 'Stereophonics' (U.S. Plant Pat. No. 15,535) in plant habit and growth rate. However, in side-by-side comparisons in Chichester, West Sussex, United Kingdom, under commercial practice, plants of the new *chrysanthemum* variety 'Bridal Time' differed from plants of 'Stereophonics' in the following characteristics:

1. The new variety 'Bridal Time' produces large white straight blade single flowers whereas 'Stereophonics' produces white spatulate single flowers.

2. Plants of the new variety 'Bridal Time' have similar size inflorescence when compared with plants of 'Stereophonics'.
3. Plants of the new variety 'Bridal Time' have a slightly quicker response than the plants of the variety 'Stereophonics'.

BRIEF DESCRIPTION OF ILLUSTRATIONS

Typical specimens of the plant and flowers for the new *Chrysanthemum* variety 'Bridal Time' are shown in the accompanying digital photograph. The colors shown are as true as possible within the usual limits of this kind of illustration.

FIG. 1 is a whole plant view of the new variety 'Bridal Time' grown in a pot. The plant shown in the illustration is 52 days from the commencement of Short Days.

DETAILED BOTANICAL DESCRIPTION

The following description of the new *Chrysanthemum* variety 'Bridal Time' is of plants grown in a greenhouse in Chichester, West Sussex, United Kingdom, in the month of September. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 5,000 to 6,000 foot candles. The plants respond well to the use of growth retardant, such as one B9 treatment at about 2 grams per liter. To produce a commercial product the plants may be pinched once with the center bud removed. The typical container size for commercial growth is 1 liter. It has been observed that the shelf life of the new variety is about 28 days with a response time of about 7 weeks. The new variety is suitable for growth in a temperature range of 15° C. to 25° C.

The following description is with respect to a plant produced as pot. In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 20.
Width (cm): 32.
Stem:
- *Length* (*cm*).—6.5.
- *Diameter* (*cm*).—0.5.
- *Texture.*—Slightly pubescent.
- *Color.*—139C.

Branching characteristics: Upright and free branching.
Lateral branches:
- *Length* (*cm*).—12.
- *Diameter* (*cm*).—0.5.
- *Texture.*—Slightly pubescent.

Number of breaks from pinch: 5.
Response time: 49 days.
Vigor: Medium to tall.
Shelf life: 28 days.
Life of blooms: 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking unrooted cuttings. The plants were grown for 2 weeks in Long Day conditions (20 hours of light) and then transferred to Short Day conditions (13 hours of dark).
Propagation:
- *Type.*—Vegetative propagation via stem cuttings.
- *Time to rooting.*—14 days with soil temperatures of 18° C.
- *Rooting habit.*—After 7 days, the first roots emerge and form root primordia. In 14 Long Days, a complete root system is developed.

Foliage

Number of leaves per lateral branch: 12.
Compound or single: Single.
Arrangement of leaves: Alternate.
- *Shape of leaf.*—Typically 5 lobed.
- *Size of leaf.*—Width (cm): 5 Length (cm): 9.
- *Leaf apex.*—Acute.
- *Base.*—Obtuse.
- *Attachment.*—Petioled.
- *Aspect.*—Slightly undulating.
- *Margin.*—Palmately lobed.
- *Surface characteristics.*—Top: Slightly pubescent. Bottom: Pubescent.

Petiole:
- *Color.*—137C.
- *Length* (*cm*).—2.
- *Diameter* (*cm*).—0.3.

Venation:
- *Color.*—Upper side: 138B. Under side: 139D.

Color:
- *Mature leaf, upper side.*—137A; under side: 139C.
- *Young leaf, upper side.*—139A; under side: 137B.

Flower

Flower appearance: Matte.
Flower type: Single.
Flower form: Slightly cupped.
Flower shape: Circular.
Flowering habit: Cyme.
Number of blossoms per branch: 5.
Typical and observed flowering season: January to December.
Inflorescence form: Cyme.
- *Depth of fully expanded blossoms* (*cm*).—1.5.
- *Diameter of fully expanded blossoms* (*cm*).—8.

Phyllaries:
- *Number.*—14.
- *Color.*—137B.
- *Length* (*cm*).—0.8.
- *Width* (*cm*).—0.2.
- *Texture/appearance.*—Pubescent.

Peduncle:
- *Length* (*cm*).—12.
- *Diameter* (*cm*).—0.5.
- *Angle from stem* (*degrees*).—20.
- *Color.*—137B.
- *Surface.*—Slightly pubescent.

*Habit.*—Slightly undulating.
*Strength.*—Moderately strong.

Pedicel:
*Length.*—Terminal (cm): 3.5; lateral (cm): 4.5.
*Diameter* (*cm*).—0.2.
*Color.*—137B.
*Surface.*—Slightly pubescent.
*Habit.*—Slightly undulating.
*Strength.*—Moderately strong.

Ray florets:
*Form/shape.*—Straight with parallel edges.
*Texture/appearance.*—Matte.
*Number per flower.*—22.
*Length* (*cm*).—4; Width (cm): 1.
*Apex.*—Rounded.
*Base.*—Tapered.
*Margin.*—Entire.

Disc florets:
*Form/shape.*—Cylindric.
*Texture/appearance.*—Shiny.
*Number per flower.*—>250.
*Length* (*cm*).—0.5; Width (cm): 0.1.
*Diameter of disc* (*cm*).—1.5.

Fragrance: None.

Flower bud (at onset of color):
*Length* (*cm*).—1.
*Diameter* (*cm*).—1.
*Form/shape.*—Globular.

General flower color:
1. *Ray florets, upper side.*—Immature: 155D. Mature: 155D. Older/Fading: 155D.
2. *Ray florets, under side.*—Immature: 158C. Mature: 155A. Older/Fading: 155A.
3. *Disc florets.*—Immature: 143A. Mature: 143C. Older/Fading: 144C.
4. *Bud.*—157A.

Flower progression with age: The flower form and color does not change with age.

Reproductive Organs

Gynoecium present on Ray and Disc florets.

Ray florets per individual flower: Pistillate.
*Pistil number.*—22.
*Stigma color.*—154A.
*Stigma shape.*—Forked.
*Style color.*—154B.
*Style length* (*cm*).—0.3.

Disc florets per individual flower: Pistillate.
*Pistil number.*—>200.
*Stigma color.*—154A.
*Stigma shape.*—Forked.
*Style color.*—154B.
*Style length* (*cm*).—0.3.

Androecium not observed.

Fruit and seeds: None observed to date.

What is claimed is:

1. A new and distinct variety of *Chrysanthemum* plant, substantially as described and illustrated herein.

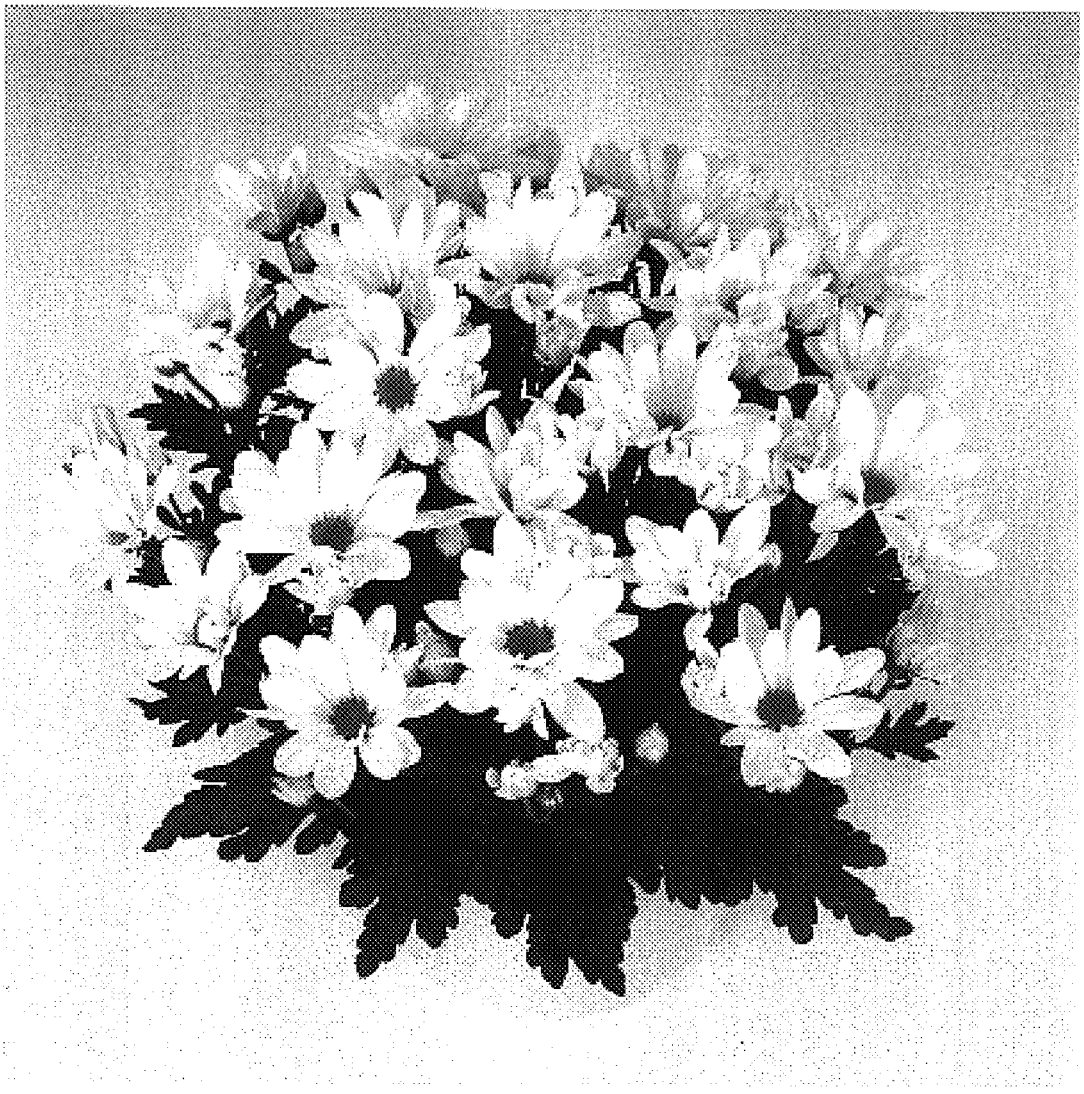

* * * * *